(12) United States Patent
Liu et al.

(10) Patent No.: US 10,045,954 B2
(45) Date of Patent: Aug. 14, 2018

(54) USE OF NOVEL ANTI-HPV PHARMACEUTICAL PREPARATION

(71) Applicant: INSTITUTE OF BIOMEDICAL ENGINEERING, CHINESE ACADEMY OF MEDICAL SCIENCE, Tianjin (CN)

(72) Inventors: Tianjun Liu, Tianjin (CN); Shuai Meng, Tianjin (CN); Lihui Zhao, Tianjin (CN); Ge Hong, Tianjin (CN)

(73) Assignee: INSTITUTE OF BIOMEDICAL ENGINEERING, CHINESE ACADEMY OF MEDICAL SCIENCE, Tianjin (CN)

( * ) Notice: Subject to any disclaimer, the term of this patent is extended or adjusted under 35 U.S.C. 154(b) by 0 days.

(21) Appl. No.: 15/037,052

(22) PCT Filed: Jul. 14, 2014

(86) PCT No.: PCT/CN2014/082148
§ 371 (c)(1),
(2) Date: May 17, 2016

(87) PCT Pub. No.: WO2015/070630
PCT Pub. Date: May 21, 2015

(65) Prior Publication Data
US 2016/0279081 A1    Sep. 29, 2016

(30) Foreign Application Priority Data

Nov. 18, 2013  (CN) .......................... 2013 1 0589439

(51) Int. Cl.
| | |
|---|---|
| *A61K 31/167* | (2006.01) |
| *A61K 9/00* | (2006.01) |
| *A61K 9/06* | (2006.01) |
| *A61K 9/12* | (2006.01) |
| *A61K 9/20* | (2006.01) |
| *A61K 9/48* | (2006.01) |
| *A61K 47/06* | (2006.01) |
| *A61K 47/08* | (2006.01) |
| *A61K 47/22* | (2006.01) |
| *A61K 47/26* | (2006.01) |
| *A61K 47/32* | (2006.01) |

(52) U.S. Cl.
CPC .......... *A61K 31/167* (2013.01); *A61K 9/0019* (2013.01); *A61K 9/0053* (2013.01); *A61K 9/06* (2013.01); *A61K 9/12* (2013.01); *A61K 9/2013* (2013.01); *A61K 9/2031* (2013.01); *A61K 9/2054* (2013.01); *A61K 9/2059* (2013.01); *A61K 9/4858* (2013.01); *A61K 9/4866* (2013.01); *A61K 47/06* (2013.01); *A61K 47/08* (2013.01); *A61K 47/22* (2013.01); *A61K 47/26* (2013.01); *A61K 47/32* (2013.01)

(58) Field of Classification Search
CPC ..... A61K 31/167; A61K 9/4858; A61K 47/22
See application file for complete search history.

(56) References Cited

FOREIGN PATENT DOCUMENTS

| | | |
|---|---|---|
| CN | 102475719 A | 5/2012 |
| CN | 103588660 A | 2/2014 |
| JP | 2009502985 A | 1/2009 |
| JP | A 2012167103 A | 9/2012 |
| WO | WO 01/80901 A2 | 11/2001 |
| WO | WO 2013/146435 A | 10/2013 |

OTHER PUBLICATIONS

Bhawar et al (Pharmacologyonline, 2010, 1, 1054-1067).*
Czelusta et al (BioDrugs, May 1999, 11 (5), 319-332).*
Chemical Biology & Drug Design, Zrinka Rajic et al., Feb. 5, 2009, vol. 73, Issue 3, p. 328-338.
Modulation of a-interferon's antiviral and clinical effects by aspirin, acetaminophen, and prednisone in healthy volunteers (C Hendrix et al.) Antiviral Research, vol. 28, No. 2, Oct. 1995, pp. 121-131.

* cited by examiner

*Primary Examiner* — Sudhakar Katakam
(74) *Attorney, Agent, or Firm* — Dragon Sun Law Firm, P.C.; Jinggao Li, Esq.

(57) ABSTRACT

The invention discloses a use of paracetamol and a pharmaceutical preparation containing the same in preparation of anti-HPV drugs. The novel anti-HPV pharmaceutical preparation of the invention has a significant anti-HPV effect and low toxicity, and can be used for preventing and treating clinical symptoms caused by HPV infection, especially common warts, plane warts, plantar wart, vulvar cancer, penile neoplasms, anal carcinoma, prostate cancer, bladder cancer, cervical cancer, rectal cancer, oral cancer, tonsil cancer and the like.

3 Claims, No Drawings

USE OF NOVEL ANTI-HPV PHARMACEUTICAL PREPARATION

CROSS-REFERENCE TO RELATED APPLICATIONS

This application claims priority from PCT Application No. PCT/CN2014/082148, filed Jul. 14, 2014 and CN Application No. CN201310589439.8, filed Nov. 18, 2013, the contents of which are incorporated herein in the entirety by reference.

FIELD OF THE INVENTION

The invention pertains to the field of pharmaceutical technology, and in particular relates to a use of paracetamol and a pharmaceutical preparation containing the same in the anti-HPV aspect.

BACKGROUND OF THE INVENTION

The human papilloma virus (HPV) is a spherical DNA virus which is human-human transmissible[1]. Currently, scientists have successfully separated more than 130 species of HPV subtypes, each of which has a different clinical manifestation form. Generally, an HPV infection causes proliferation of squamous epithelial cells on a genital organ, an anus, pharynx oralis and esophageal mucosa, which are manifested as common warts, plane warts, plantar wart and the like. A serious HPV infection even can cause malignant tumors, including vulvar cancer, penile neoplasms, anal carcinoma, prostate cancer, bladder cancer, cervical cancer, rectal cancer, oral cancer, tonsil cancer and the like.

In 1995, it was found in the research data of epidemiology provided by International Agency for Research on Cancer (IARC) that, high-risk HPV16 and HPV18 were main causes of female cervical cancers and were extremely infectious[2]. In China, almost all of the cervical cancers are related to the infection of HPV[3].

According to statistics of global venereal diseases, genital warts caused by HPV infection account for 15-20%. Moreover, the result of an investigation related to the epidemic situation of HPV as provided by the USA national health and nutrition research subject in 2003-2004 showed that, the total infection rate of HPV in a genital tract of a woman aged from 14 to 59 is 26.8%[4-5].

A method currently used for treating HPV clinical symptoms includes:

(1) A physical therapy aimed to remove a tumor body visible to the naked eye and a subclinical infection, such as a laser, microwave, surgical excision (gynecological LEEP knife, etc.), photodynamic therapy and the like. The physical therapy is mainly directed to a tumor caused by viruses, rather than eradication of viruses at the source;

(2) A drug therapy, wherein currently there is no antiviral drug specific to the virus, and thus generally a cytotoxic drug (including 0.5% of podophyllotoxin tincture, 50% of trichloroacetic acid, fluorouracil ointment, and the like) is used clinically for adjuvant therapy. Podophyllin and the like have a certain corrosivity, and thus it needs to protect surrounding healthy tissues from them, otherwise it is easy to cause implantation of surrounding healthy tissues; and since the aforementioned drugs have strong toxicity and cannot radically cure HPV, the possibility of recrudescence is very large;

(3) An immunization therapy directed to reducing recrudescence and rapid focus clearance, including interferons, interleukins, thymosins, transfer factors, BCG vaccines, isotretinoin, autovaccines and the like, with disadvantages of high price, poor stability, and complex treatment procedure; and (4) Therapeutic vaccines: the prophylactic anti-HPV vaccines only include Gardasil available from Merck and Cervarix available from GlaxoSmithKline; however, existing anti-HPV vaccines still have certain disadvantages, such as being only directed to certain virus subtypes, being expensive, having a not wide enough range of target population (females aged 13-26), having a short effective immune period (an effective time of 3-5 years), and the like, which hinder the effective promotion of current vaccines[6].

Paracetamol is a commonly-used antipyretic and pain-relief drug, which is generally used for curing a fever, an arthralgia, a neuralgia, a migraine and a cancer pain, and for relieving pains after surgery. It was found by the research group during screening of antiviral drugs that, the paracetamol had a relatively strong anti-HPV16 activity. Based on this research results, we prepared a series of pharmaceutical preparations containing paracetamol, and they were used in treatment of HPV16. As compared with the previously used treating method, the invention provides a pharmaceutical preparation containing paracetamol, which has advantages such as being simply prepared, having a low production cost, having a significant anti-HPV effect, and the like. Therefore, it is of great practical significance to develop them into a clinical medicine for treating HPV.

REFERENCES

[1] Woodman C B. Collins S I. Young L S. The natural history of cervical HPV infection: unresolved issues[J]. Nat Rev Cancer, 2007. 7(1): 11-22.

[2] IARC Working Group on the Evaluation of Carcinogenic Risks to Humans. Human papillomaviruses[J]. IARC Monogr Eval Carcinog Risks Hum, 1995, 64: 1-378.

[3] You-lin Qiao, Epidemiology of HPV Infection and Cervical Cancer and Perspective of HPV Vaccination in Chinese Women[J]. Chinese Journal of Epidemiology, 2007, 28(10): 937-940.

[4] Ben Wang, Zheng-Ai Xiong, Current Situation and Research Progresses of HPV Prophylactic Vaccines[J]. Guangdong Medical Journal, 2011, 32(4): 530-532.

[5] Li-Xia He, Jun-Yong He, Jian-Lu Pu, et. al. People's present Cognition Status of HPV Infection[J]. Medical Journal of West China, 2012, 24(8): 1643-1644.

[6] Lei Wan, Jian-Ping Wan, Yan-ling Zhang, et. al. Clinical Analysis of the Trend of Carcinoma of the Cervix in Young Women[J]. Chinese Journal of Clinical Oncology, 2004, 31(10): 547-549.

SUMMARY OF THE INVENTION

A first object of the invention is to provide a use of paracetamol as an anti-HPV drug.

A second object of the invention is to provide a use of a pharmaceutical preparation containing an effective dose of paracetamol as an anti-HPV drug.

The technical solution of the invention is summarized as follows:

The paracetamol and paracetamol pharmaceutical preparation of the invention can be used for preventing and treating clinical symptoms caused by HPV infection, especially common warts, plane warts, plantar wart, vulvar cancer, penile neoplasms, anal carcinoma, prostate cancer, bladder cancer, cervical cancer, rectal cancer, oral cancer, tonsil cancer and the like.

A novel anti-HPV pharmaceutical preparation of the invention is using paracetamol alone or in combination with other drugs, wherein a pharmaceutically acceptable drug carrier is added, such that the weight percentage of the paracetamol is 0.1-40% based on the total weight of the pharmaceutical preparation, and the paracetamol is prepared into any clinically acceptable dosage form, including tablets, pills, capsules, granules, suspensions, aerosols, oral liquid, ointments, gels, patches, injections, infusion solutions, freeze-dried injection products, and sustained or controlled release preparations.

The paracetamol of the invention is a compound as shown in the formula below:

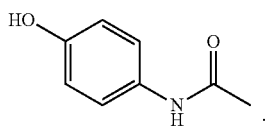

The pharmaceutically acceptable carrier includes a conventional diluting agent (e.g., at least one of water for injection, microcrystalline cellulose, and the like), a filling agent (e.g., at least one of mannitol, sucrose, lactose, polyethylene glycol, Tween 80, sorbitol, menthol, liquid paraffin, vaseline, stearic acid, glycerin monostearate, lanum, mineral oil, DMSO, and the like), an adhesive agent (e.g., at least one of carbomer, Arabic gum, starch, cellulose, gelatin, polyvinylpyrrolidone, polyacrylamide, and the like), a disintegrating agent (e.g., at least one of sodium carboxymethyl starch, croscarmellose sodium, hydroxypropyl methylcellulose, low-substituted hydroxypropyl cellulose, and the like), a lubricating agent (e.g., at least one of talcum powder, magnesium stearate, calcium stearate, solid polyethylene glycol, lecithin, silicon dioxide, micropowder silica gel, and the like), a wetting agent (e.g., at least one of propylene glycol, glycerin, ethyl alcohol, and the like), a stabilizing agent (e.g., at least one of disodium ethylenediaminetetraacetic acid, sodium thiosulfate, sodium metabisulfite, sodium sulfite, sodium hydrogensulfite, ethanolamine, sodium bicarbonate, sodium acetate, nicotinamide, vitamin C, and the like), an osmolality adjusting agent (e.g., at least one of sodium chloride, glucose, and the like), a pH adjusting agent (e.g., at least one of triethanolamine, sodium hydroxide, sodium citrate, and the like), and a preservative (e.g., at least one of chlorobutanol, Nipagin ester, ethylparaben, benzalkonium bromide, and the like). The aforementioned adjuvants may be of common dosages, and are mixed with paracetamol according to a common proportion. When the dosage of paracetamol is determined, the proportions of respective pharmaceutic adjuvants can be adjusted appropriately if desired.

The pharmaceutical preparation of the invention contains 1-500 mg of paracetamol per dose, and the administration amount thereof can be adjusted according to routes of administration, ages and weights of patients, types and severity of diseases and many other factors, and can be appropriately changed according to manifestations of clinical cases. The daily dose is generally 1-50 mg/kg, preferably 10-40 mg/kg, and most preferably 20-30 mg/kg.

DETAILED DESCRIPTION OF PARTICULAR EMBODIMENTS OF THE INVENTION

Example 1 Preparation of Paracetamol

To a 500 mL reaction flask is added 10 g paraaminophenol, 9.5 g acetic anhydride, and 150 mL dichloromethane, and the mixture is stirred at room temperature for 2 h, and then heated to reflux for 4 h. The reaction is cooled, and the solvent is evaporated off under reduced pressure. The solvent is recrystallized from 40 mL ethyl alcohol, to provide a product of 13.3 g, with a yield of 95.6%.

Example 2 Tablets (Dry Method)

To 150 g paracetamol is added 75 g hydroxy propyl cellulose, 75 g sodium carboxymethyl starch, and 180 g starch, and the mixture is mixed uniformly in an equivalent incremental manner, and then dry-granulated; 20 g magnesium stearate is added, and the mixture is mixed uniformly; and pressed into tablets.

Example 3 Tablets (Wet Method)

To 300 g paracetamol is added 500 g starch, 100 g magnesium stearate, 200 g carboxymethyl cellulose, 2700 g ethyl alcohol (with a volume percentage of 70%), 2500 g microcrystalline cellulose, and 3200 g corn starch, and the mixture is mixed thoroughly with stirring and made into wet granules, dried at 60-70° C. for 2-4 hours, and pressed into tablets. The adjuvants used as excipients for press forming the tablets include magnesium sulfate, corn starch and talcum powder.

Example 4 Pills

To 100 g paracetamol is added 900 g polyethylene glycol, melted by heating at 90° C. such that the raw materials and the adjuvants are well melt blended. The melt is added dropwise into a dimethyl silicone oil receiving liquid, and cooled naturally to form dropping pills each containing 100-200 mg paracetamol.

Example 5 Capsules

To 300 g paracetamol is added 20 g magnesium stearate, 200 g carboxymethyl cellulose and 480 g microcrystalline cellulose, and the mixture is mixed thoroughly with stirring and made into wet granules. The resulting wet granules are directly dried at 60-70° C. for 2-4 hours, then filled into empty capsule shells, with each capsule containing 200 mg paracetamol.

Example 6 Granules

To 600 g paracetamol is added 20 g magnesium stearate, 180 g carboxymethyl cellulose and 200 g microcrystalline cellulose, and the mixture is mixed thoroughly with stirring, and made into granules by passing through a 12-14 mesh screen. The granules are dried at 60-70° C. for 2-4 hours, such that 200 mg paracetamol is contained per gram of the granules.

Example 7 Suspensions

To 20 g paracetamol is added 420 g pure water, 390 g glycerin, 70 g sorbitol and 100 g propylene glycol, and the mixture is suspended uniformly in an aqueous carrier.

Example 8 Aerosols

To 1 g paracetamol dissolved in propylene glycol is added 0.5 g vitamin C and 0.2 mL chlorobutanol, and the mixture is mixed uniformly to form a transparent solution, and loaded into a pressured vessel together with a pressurized nitrogen gas by specification.

Example 9 Aerosols

To 50 g paracetamol is added 200 g glycerin, 100 g propylene glycol, 1 g Tween 80, 2 g menthol and 100 g pure water, and the mixture is stirred uniformly, and loaded into a vessel equipped with a nozzle, so as to obtain the product.

Example 10 Oral Liquid

To 50 g paracetamol is added 7.45 kg pure water and 2.5 kg edible sugar, and the mixture is dissolved by stirring, and sterilized separately, so as to obtain the product.

Example 11 Ointments (Oleaginous Base)

500 g vaseline and 400 g liquid paraffin are melted respectively by heating, filtered while being still hot so as to remove impurities, and then heated to 150° C. for about 1 h for sterilization and moisture removal, and cooled naturally; to 100 g paracetamol placed in a mortar is added appropriate amount of liquid paraffin, and the mixture is ground into a paste. To the paste is added vaseline in several portions, and the mixture is ground uniformly to obtain the product.

Example 12 Ointments (o/w Type Emulsifier Base)

A beaker is charged with 100 g stearic acid, 70 g glyceryl monostearate, 70 g white vaseline and 60 g liquid paraffin, is heated in a water bath to about 80° C., and melted with stirring. Another small beaker is charged with 0.5 g Tween 80 and 600 mL distilled water, heated in a water bath to about 80° C., and stirred uniformly. At the same temperature, the aqueous phase is added into the oleic phase in fine streams, and the mixture is stirred clockwisely in a water bath continuously to form a milky semisolid, and then the semisolid is stirred at room temperature until being almost congealed. 100 g paracetamol is placed on an ointment slab and in a mortar, and the prepared O/W type emulsifier base is added in several portions, and the mixture is ground uniformly to obtain the product.

Example 13 Gels 10 g carbomer 934 is poured into an appropriate amount of distilled water such that the carbomer 934 is swelled slowly, and 100 g glycerin is added and stirred to form a transparent gel base. Additionally, menthol dissolved in ethyl alcohol and 10 g boric acid dissolved in appropriate amount of water are combined and stirred uniformly. 10 g paracetamol is poured into the mixture while being stirred, and the pH of the reactants is adjusted to pH 4.5-5.5 by triethanolamine, water is added until the volume is 1000 mL, then the resultant is stirred uniformly and subpackaged to obtain the product.

Example 14 Patches 4 g carbomer is weighed and heated to 60° C. together with propylene glycol, Tween-80 and distilled water according to a proportion of 10:20:3:12 under stirring for 20 min, 1 g paracetamol is added, and the mixture is stirred uniformly; and coated on a lining cloth in several portions until a desired thickness is reached, the coated cloth is dried in the air or in an oven, and then clipped according to a preparation specification so as to obtain the product.

Example 15 Sustained or Controlled Release Tablets

To 300 g paracetamol is added 70 g hydroxypropyl methyl cellulose, 250 g carboxymethyl cellulose, 370 g ethyl alcohol (with a volume percentage of 70%), 10 g magnesium stearate, and the like, and the mixture is mixed thoroughly with stirring, made into wet granules, dried at 60-70° C. for 2-4 hours, and pressed into tablets.

Example 16 Sustained or Controlled Release Tablets

To 600 g paracetamol is added 280 g hydroxypropyl methyl cellulose, 30 g stearic acid, 80 g lactose, 10 g magnesium stearate, and the mixture is mixed thoroughly with stirring, made into granules through a dry method, and pressed into tablets, each containing 100 mg paracetamol.

Example 17 Injections 3 g vitamin C is dissolved by the addition of 2800 mL injection water, and heated to 30° C.-40° C., to the mixture is added 90 g paracetamol and 18 g Tween-80, and the mixture is cooled to room temperature, and to the mixture is added 27 g sodium chloride. The pH value of the mixture is adjusted to 7.0-7.5 by a solution containing 5% of sodium citrate, and the mixture is diluted with the injection water to a constant volume of 3000 mL; the preparation is subpackaged in ampoule bottles according to a preparation specification, with a volume of 3-5 mL per bottle, and the ampoule bottles are heat sealed; the bottles are sterilized under a circulating steam of 100° C. for 30 min, so as to obtain the product.

Example 18 Injections

To a solution prepared from 10 g paracetamol, 50 g glucose and 940 g injection water is dropwise added an aqueous hydrochloric acid solution with a volume ratio of 1:1, so as to adjust the pH value to 4.0. To the solution is added 1 g activated carbon, and the mixture is boiled under stirring for 30 minutes, then the activated carbon is filtered off, and then the solution is sterilized by filtering through a 0.22 μm filter membrane, so as to obtain a clear sterile liquid. The liquid is encapsulated and hot-pressing sterilized at 115° C. for 30 minutes, so as to obtain the product.

Example 19 Freeze-Dried Powder Injection 45 g paracetamol and 40 g mannitol are added into 910 g injection water, and are dissolved under stirring. The pH of the solution is adjusted to 6.2 by dropwise adding an aqueous hydrochloric acid solution with a volume ratio of 1:1. Then 5 g activated carbon for refinement of injection is added, and the mixture is stirred at room temperature for 20 minutes, then the activated carbon is filtered off, and then the solution is sterilized by filtering through a 0.22 μm filter membrane, so as to obtain a clear sterile liquid. The liquid is encapsulated into 5 mL tube vials, each tube vial containing 3 mL liquid. The tube vials are freeze-dried in a vacuum freeze drier to obtain the product.

Example 20 Infusion Solutions

To 10 g paracetamol is added 4 g polyethylene glycol, 3 g lecithin, 6 g sodium acetate, 6 g sodium sulfite and 900 g sodium chloride, and the mixture is dissolved in injection water, filtered, encapsulated, sterilized, and packaged to obtain the product.

Example 21 Infusion Solutions

To 10 g paracetamol is added 4 g polyethylene glycol, 4 g lecithin, 4 g sodium acetate, 8 g sodium sulfite and 5 kg glucose, and the mixture is dissolved in injection water, filtered, encapsulated, sterilized, and packaged to obtain the product.

Each preparation unit contains 50 mg paracetamol, and can be used for intramuscular injection or intravenous injection, with a dose of 1-2 times a day, each time administrating 1-2 preparation units.

Example 22

The evaluation of in vitro antiviral evaluation of paracetamol and paracetamol pharmaceutical preparation obtained from examples 1-21 includes the following steps:

(1) Cytotoxicity assay: human cervical cancer Caski cells (HPV16 positive) at an exponential phase cultured through a conventional culturing method is digested by a trypsase, such that the attached cells are detached. The cells are suspended in a liquid medium containing 10% of fetal bovine serum, and are cultured by inoculating in a 96-well plate, each well containing $1 \times 10^5$ cells. The cells are incubated in a $CO_2$ incubator for 24 h to make the cells be attached. labeled amount of paracetamol or paracetamol pharmaceutical preparation prepared from examples 1-21 is dissolved in DMSO used for cell culture, and then the solution is diluted with the liquid medium into a series of drug culture media with increasing concentrations, wherein the concentrations are sequentially 25, 50, 100, 200 and 400 µg/mL. The culture medium is decanted, 100 µL drug culture medium formulated according to a multiple relationship is added into the administered group, while a culture medium is used instead of the drug solution for the control group, wherein four vice holes are used at each concentration, and the cells are incubated in a $CO_2$ incubator for 72 h. The median toxic concentration ($TC_{50}$) and maximal atoxic concentration ($TC_0$) are calculated based on a Reed-Muench method, by using a MTT method.

(2) Efficacy evaluation of paracetamol and the pharmaceutical preparation containing paracetamol by using Caski cells as a model: a drug culture medium of $TC_0$ is prepared from a liquid medium according to the labelled amount of paracetamol or the pharmaceutical preparation containing paracetamol, cells treated with the drug culture medium are cultured for 48 hours, and then the total RNA is extracted from the cells. The total RNA is reverse transcribed by using Oligo(dT)$_{15}$ as a primer. Finally using the cDNA as the template, E6 and E7 as the target gene, and β-actin as a reference gene, the gene expression level variations of HPV16 E6 and E7 mRNA are determined by adoption of a Real-time PCR method after the paracetamol or the pharmaceutical preparation containing the same acts on the Caski cells, so as to determine the inhibitory activity of the pharmaceutical preparation on virus HPV16 (the assay results are as shown in table 1).

TABLE 1

Cytotoxicity Assay of paracetamol and pharmaceutical preparation containing the same, and the effects thereof on expression of HPV 16 E6/E7 mRNA

| Designation | $TC_{50}$ (µg/mL) | $TC_0$ (µg/mL) | HPV E6 mRNA (%) | HPV E6 mRNA (%) |
|---|---|---|---|---|
| Example 1 | >200 | 200 | 74.80 | 65.79 |
| Example 2 | >200 | 200 | 70.07 | 62.16 |
| Example 3 | >200 | 200 | 73.04 | 64.15 |
| Example 4 | >200 | 200 | 72.08 | 63.17 |
| Example 5 | >200 | 200 | 71.00 | 61.19 |
| Example 6 | >200 | 200 | 73.27 | 64.36 |
| Example 7 | >200 | 200 | 72.24 | 63.35 |
| Example 8 | >200 | 200 | 71.28 | 62.37 |
| Example 9 | >200 | 200 | 74.20 | 61.39 |
| Example 10 | >200 | 200 | 70.20 | 65.32 |
| Example 11 | >200 | 200 | 72.40 | 63.51 |
| Example 12 | >200 | 200 | 71.47 | 62.56 |
| Example 13 | >200 | 200 | 74.47 | 61.56 |
| Example 14 | >200 | 200 | 70.43 | 65.54 |
| Example 15 | >200 | 200 | 73.42 | 64.51 |
| Example 16 | >200 | 200 | 71.60 | 62.75 |
| Example 17 | >200 | 200 | 74.64 | 61.76 |
| Example 18 | >200 | 200 | 70.67 | 65.73 |
| Example 19 | >200 | 200 | 73.60 | 64.71 |
| Example 20 | >200 | 200 | 72.68 | 63.77 |
| Example 21 | >200 | 200 | 74.82 | 64.93 |

What is claimed is:

1. A method of inhibiting HPV16 virus by administering an effective amount to a patient infected with HPV16 a pharmaceutical composition comprising a paracetamol and a carrier, wherein the paracetamol is a compound of the following formula:

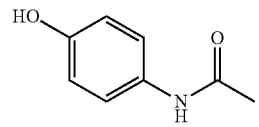

wherein said compound inhibits the HPV16 itself, wherein
the effective amount of the pharmaceutical composition contains the carrier such that a weight percentage of the paracetamol is 0.1-40% based on the total weight of the pharmaceutical composition;
the paracetamol is prepared into one form selected from tablets, pills, capsules, granules, suspensions, aerosols, oral liquid, ointments, gels, patches, injections, infusion solutions, freeze-dried injection products, and sustained or controlled release preparations; and
the pharmaceutical preparation of the pharmaceutical composition contains 1-500 mg of the paracetamol per dose, and a daily dose of the paracetamol is 1-50 mg per kilogram of a user in weight.

2. The method of claim 1, wherein the HPV16 causes cervical cancer.

3. The method of claim 1, wherein when efficacy evaluation of the paracetamol and the pharmaceutical preparation containing the paracetamol by using Caski cells as a model, the Caski cells treated with the paracetamol as a culture medium at a maximal atoxic concentration, the paracetamol alone has an inhibitory activity on the HPV16 virus.

* * * * *